June 21, 1966 D. H. MOREY, JR Plant Pat. 2,645
ROSE PLANT
Filed June 14, 1965
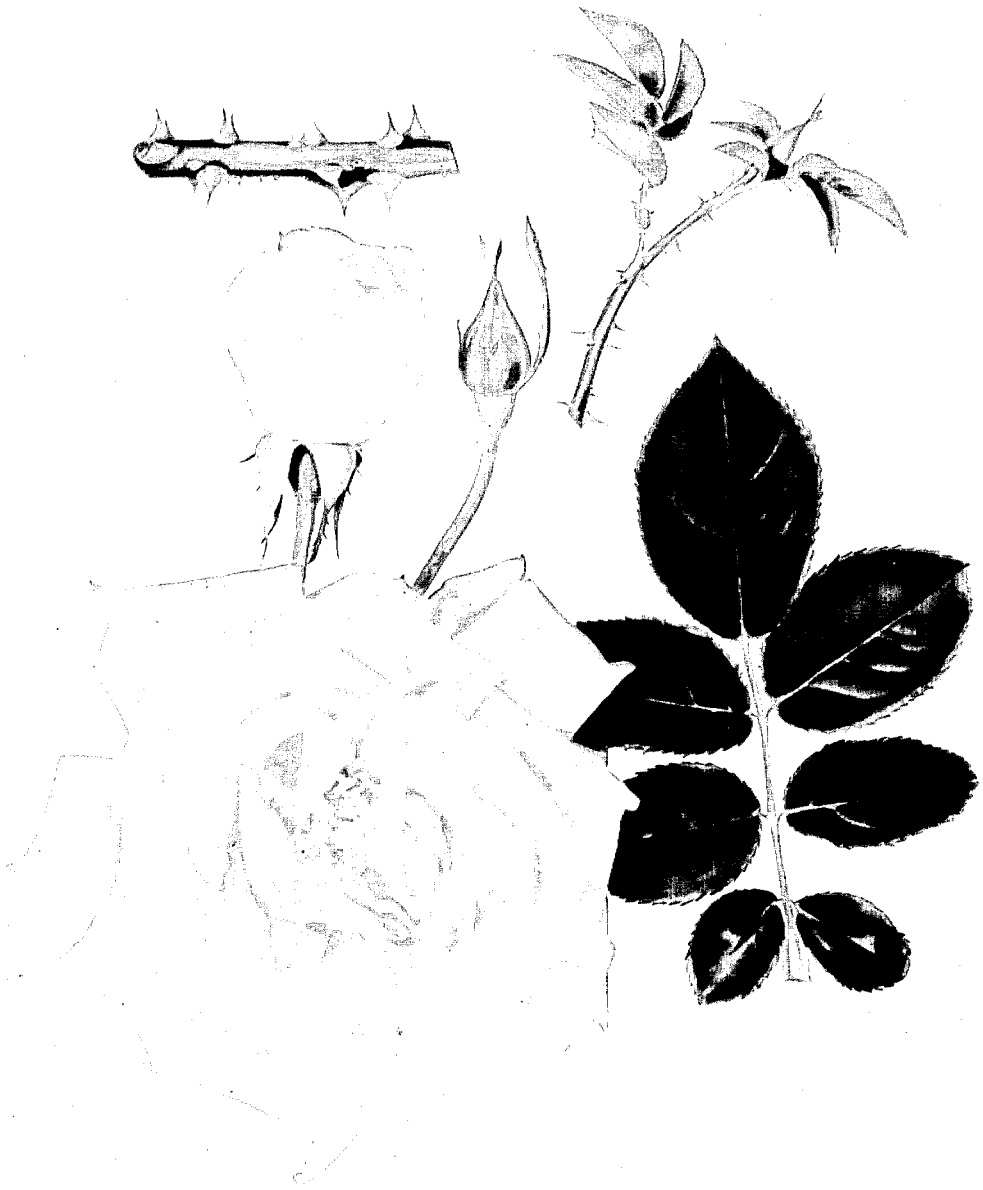
Inventor.
Dennison H. Morey, Jr.
By: Robb & Robb
Attorneys.

United States Patent Office

Plant Pat. 2,645
Patented June 21, 1966

2,645
ROSE PLANT

Dennison H. Morey, Jr., Pleasanton, Calif., assignor to Jackson & Perkins Company, Newark, N.Y., a corporation of New York

Filed June 14, 1965, Ser. No. 463,975
1 Claim. (Cl. Plt.—20)

The present invention relates to a new and distinct variety of rose plant of the hybrid tea class, which was originated by me by crossing the variety "Independence" (Plant Patent No. 1,036) with the variety "Chrysler Imperial" (Plant Patent No. 1,167).

The primary objective of this breeding was to produce a new and improved rose variety comparable to the parent variety "Chrysler Imperial," but which bears flowers of a lighter red color. This objective was fully achieved, along with other desirable improvements, as evidenced by the following unique combination of characteristics which are outstanding in the new variety and which distinguish it from its parents, as well as from all other varieties of which I am aware:

(1) A free blooming habit;
(2) Long, strong and upright flower stems;
(3) A large flower size, with many flowers being open at a time;
(4) A distinctive and attractive general color tonality of the flowers corresponding to Scarlet-Red, lightly overcast with Spectrum Red;
(5) Long-lasting qualities of the flowers both on the plant and as cut flowers; and
(6) An Old Rose Perfume fragrance.

Asexual reproduction of my new variety by budding, as performed at Pleasanton, California, and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"Independence."
*Pollen parent.*—"Chrysler Imperial."
Classification:
*Botanic.*—Hybrid tea.
*Commercial.*—Hybrid tea.

*Flower*

(Observations made from specimens grown in a greenhouse at Newark, New York, in the early morning during the middle of the month of March.)

Blooming habit: Recurrent—continuous; has as many as 21 blooms at one time.
Bud:
*Size.*—Large.
*Form.*—Pointed; is not affected by wet or hot weather.
*Color.*—When sepals first divide—Carmine, Plate 1. When petals begin to unfurl—Carmine, Plate 1 lightly overcast with Scarlet-Red, Plate 1. When half-blown: Inside of petals—Spectrum Red, Plate 1, lightly overcast with Carmine, Plate 1; reverse of petals—Scarlet-Red, Plate 1, very lightly overcast with Carmine, Plate 1.

*Sepals.*—Smooth edge; curl back when petals begin to unfurl. Color—Inside: Pale Turtle Green, Plate 32. Outside: Cosse Green, Plate 5.
*Calyx.*—Color—Lettuce Green, Plate 5. Shape—pear. Size — large. Aspect — smooth. Odor when rubbed—none.
*Peduncle.* — Length — medium. Apsect — rough. Strength — erect; heavy. Color — Yellowish Oil Green, Plate 5.
*Opening.*—Opens up well; is not affected by adverse weather conditions.
Bloom:
*Size.*—Large. Average size when fully expanded—5 inches.
*Borne.*—Singly.
*Stems.*—Long; strong and upright.
*Form (when first open).*—Cupped. Permanence—retains its form to the end.
*Petalage.*—Double (full but open center). Number of petals under normal conditions—from 25 to 30.
*Color.*—Center of flower—Spectrum Red, Plate 1, lightly overcast with Carmine, Plate 1. Outer petals—Spectrum Red, Plate 1. Base of petals (aiglet)—Apricot Yellow, Plate 4. Inside of petals—Scarlet-Red, Plate 1, lightly overcast with Spectrum Red, Plate 1. Reverse of petals—Begonia Rose, Plate 1, very lightly overcast with Rose Red, Plate 12. General tonality from a distance—Scarlet-Red, Plate 1.
*Discoloration.*—General tonality at end of first day—Spectrum Red, Plate 1, lightly overcast with Carmine, Plate 1. Second day — Scarlet-Red, Plate 1, lightly overcast with Spectrum Red, Plate 1. Third day—Scarlet-Red, Plate 1.
Petals:
*Texture.*—Leathery; is not affected by wet or hot weather.
*Appearance.*—Inside—Velvety. Outside — satiny.
*Form.*—Round; slightly notched.
*Arrangement.*—Imbricated (regularly arranged shingle-like).
*Petaloids in center.*—Few; large.
*Persistence.*—Drop off cleanly.
*Fragrance.* — Moderate. Nature — "Old Rose Perfume" (Centifolia).
*Lasting quality.*—On the plant—long. As cut flower—long.

*Genital organs*

Stamens, Anthers: Large; many; arranged regularly around styles. Color — Ochraceous-Buff, Plate 15.
Stamens, Filaments (threads): Long. Color — Zinc Orange, Plate 15.
Pollen: Color—Pale Ochraceous-Buff, Plate 15.
Styles: Loosely separated; uneven length; medium length; thin.
Stigmas: Color—Naples Yellow, Plate 16.
Ovaries: All enclosed in calyx.
Hips: None.
Seeds: None.

*Plant*

Form: Bush.
Growth: Vigorous; upright.
Foliage: Compound of 3–5 leaflets.
*Size.*—Large.
*Quantity.*—Normal.
*Color.*—New foliage: Upper side—Oil Green, Plate 5, slightly overcast with Hay's Russett, Plate 14. Under side—Pois Green, Plate 41, lightly overcast with Madder Brown, Plate 13. Old foliage: Upper side—Spinach Green, Plate 5. Under side—Chromium Green, Plate 32.

*Shape.*—Oval pointed.
*Texture.*—Upper side—glossy. Under side—smooth.
*Ribs and veins.*—Prominent.
*Edge.*—Serrated (saw toothed).
*Serration.*—Both double and single; small.
*Leaf stem.*—Color—Courge Green, Plate 17. Under side—smooth.
*Stipules.*—Medium length; smooth.

Wood:

*New wood.*—Color—Biscay Green, Plate 17. Bark—smooth.
*Old wood.*—Color—Light Bice Green, Plate 17. Bark—smooth.

Thorns:

*Thorns.*—Quantity: On main stalks from base—many. On laterals from stalk—ordinary. Form—flat base; medium length; some straight and some hooked downward. Color (when young)—Flesh Color, Plate 14. Position—irregular.
*Prickles.*—Quantity: On main stalks—none. On laterals—none.

*Short needles.*—Quantity: On main stalks—none. On laterals—none.

I claim:

A new and distinct variety of rose plant of the hybrid tea class, substantially as herein shown and described, characterized particularly as to novelty by the unique combination of a free blooming habit, long, strong and upright flower stems, a large flower size, with many flowers being open at a time, a distinctive and attractive general color tonality of the flowers corresponding to Scarlet-Red, lightly overcast with Spectrum Red, long-lasting qualities of the flowers both on the plant and as cut flowers, and an Old Rose Perfume fragrance.

No references cited.

ANTONIO F. GUIDA, *Acting Primary Examiner.*

R. E. BAGWILL, *Assistant Examiner.*